(12) United States Patent
Insall et al.

(10) Patent No.: US 6,402,786 B1
(45) Date of Patent: Jun. 11, 2002

(54) FOUR COMPARTMENT KNEE

(75) Inventors: John N. Insall, New York, NY (US); Mark Heldreth, Mentone, IN (US); Vince Webster, Warsaw, IN (US); Steve Zawadski, Leesburg, IN (US); Roy Yoshikazu Hori, Tokyo; Kyoko Ohkuni, Shizuoka, both of (JP); Audrey Beckman, Warsaw, IN (US); William Rohr, Cincinnati, OH (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/606,608

(22) Filed: Jun. 29, 2000

Related U.S. Application Data

(62) Division of application No. 09/037,417, filed on Mar. 10, 1998, now Pat. No. 6,123,729.

(51) Int. Cl.$^7$ .................................................. A61F 2/38
(52) U.S. Cl. ................................................. 623/20.35
(58) Field of Search ........................... 623/20.35, 20.15, 623/20.14, 20.16, 20.17, 20.21

(56) References Cited

U.S. PATENT DOCUMENTS

| | | | |
|---|---|---|---|
| 4,209,861 A | | 7/1980 | Walker et al. ................ 3/1.911 |
| 4,213,209 A | | 7/1980 | Install et al. ................. 3/1.911 |
| 4,224,697 A | | 9/1980 | Murray et al. ............... 3/1.911 |
| 4,249,270 A | | 2/1981 | Bahler et al. ................ 3/1.911 |
| 4,298,992 A | | 11/1981 | Burstein et al. ............. 3/1.911 |
| 4,353,136 A | | 10/1982 | Polyzoides et al. .......... 3/1.911 |
| 4,634,444 A | | 1/1987 | Noiles .......................... 623/20 |
| 4,714,474 A | | 12/1987 | Brooks, Jr. et al. ........... 623/20 |
| 4,888,021 A | | 12/1989 | Forte et al. ................... 623/20 |
| 4,892,547 A | | 1/1990 | Brown ......................... 623/20 |
| 4,936,847 A | * | 6/1990 | Manginelli ................... 623/23 |
| 4,950,297 A | | 8/1990 | Elloy et al. ................... 623/20 |
| 4,950,298 A | | 8/1990 | Gustilo et al. ................ 623/20 |
| 4,959,071 A | | 9/1990 | Brown et al. ................. 623/20 |
| 5,007,933 A | | 4/1991 | Sidebotham et al. ......... 623/20 |
| 5,011,496 A | | 4/1991 | Forte et al. ................... 623/20 |

(List continued on next page.)

FOREIGN PATENT DOCUMENTS

| | | | | |
|---|---|---|---|---|
| EP | 0 103 697 A1 | | 3/1984 | ............ A61F/1/03 |
| EP | 0 294 298 | | 12/1988 | ................. 623/20 |
| EP | 2 701 387 | | 8/1994 | ................. 623/20 |
| FR | 2621243 | * | 4/1989 | ................. 623/20 |

OTHER PUBLICATIONS

The Genesis Total Knee System—Smith & Nephew Richards—No date available.
Orthomet, Inc—The Orthomet Axiom™ Total Knee—1993—JBJS, Jan. 1993.
Johnson & Johnson Orthopaedics Ltd.—The PFC Modular Total Knee System—British JBJS, Jan. 1991.

*Primary Examiner*—Corrine McDermott
*Assistant Examiner*—Alvin Stewart
(74) *Attorney, Agent, or Firm*—Jacque Wilson, Esq.

(57) ABSTRACT

A femoral knee implant includes a fourth compartment of articulation. The superior posterior articulating surface is achieved by first increasing the thickness of the superior posterior condylar portion of the femoral component to widen the superior posterior edge of the posterior condyle. Second, the newly created surface at the superior posterior condyle is smoothly rounded to provide an articular surface with no sharp changes in the surface contours. In one embodiment, the fourth articular compartment of this invention is provided in a one piece femoral design. In another embodiment, it is provided as a modular addition to an existing prior art femoral component. In another embodiment, the fourth compartment is combined with a posterior stabilized (PS) TKR design that includes a tibial post and cooperating femoral cam characterized by low engagement of the cam on the spine.

3 Claims, 4 Drawing Sheets

U.S. PATENT DOCUMENTS

| | | | |
|---|---|---|---|
| 5,116,376 A | 5/1992 | May | 623/20 |
| 5,147,405 A | 9/1992 | Van Zile et al. | 623/20 |
| 5,152,796 A | 10/1992 | Slamin | 623/20 |
| 5,181,925 A | 1/1993 | Houston et al. | 623/20 |
| 5,236,461 A | 8/1993 | Forte | 623/20 |
| 5,330,534 A | 7/1994 | Herrington et al. | 623/20 |
| 5,370,699 A | 12/1994 | Hoed et al. | 623/20 |
| 5,571,194 A * | 11/1996 | Gabriel | 623/18 |
| 6,005,018 A * | 12/1999 | Cicerega et al. | 523/20 |
| 6,152,960 A * | 11/2000 | Pappas | 623/20.31 |
| 6,190,415 B1 | 2/2001 | Cooke et al | |

* cited by examiner.

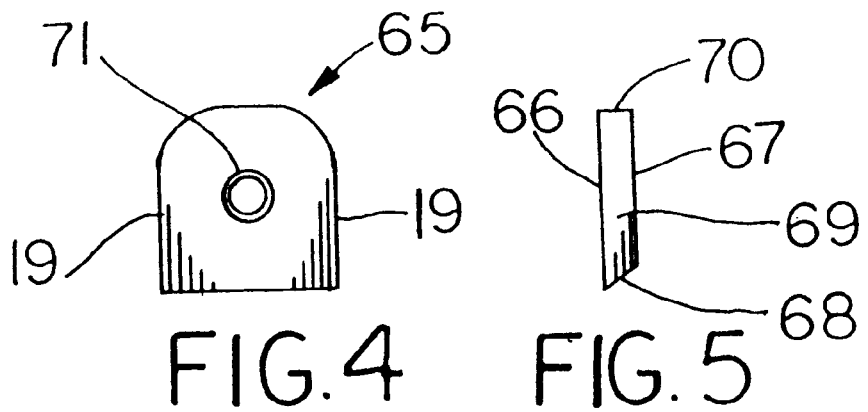
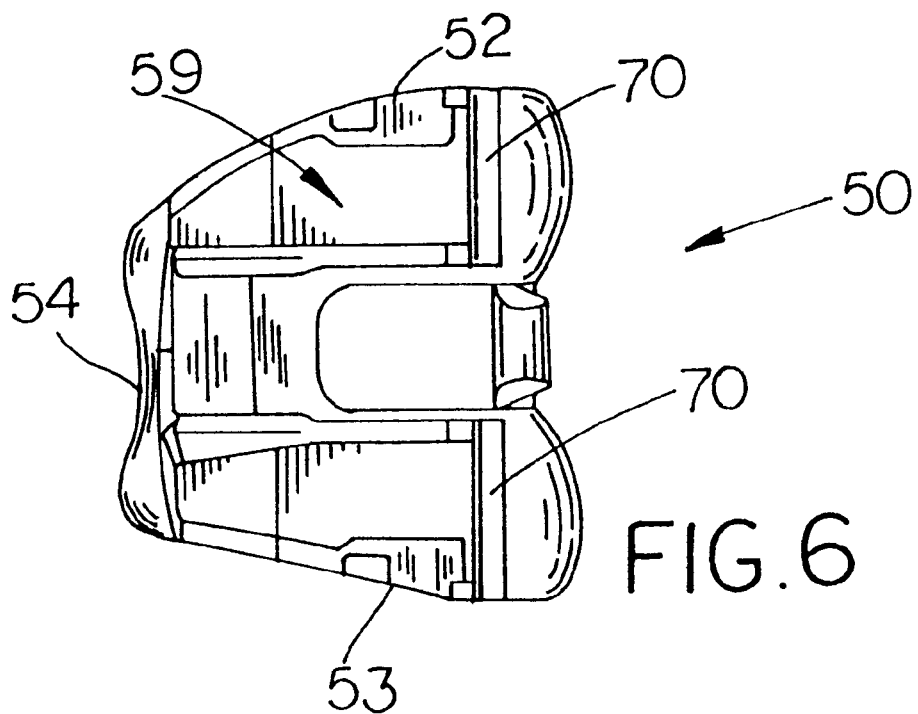
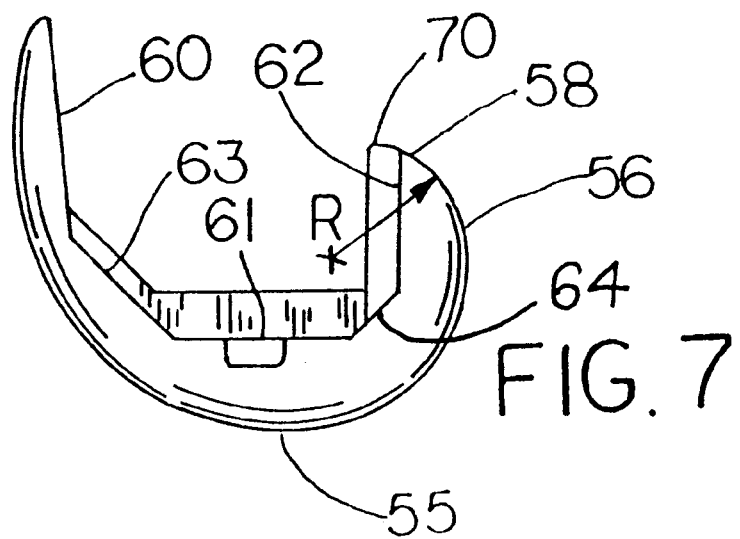

FOUR COMPARTMENT KNEE

This is a divisional of U.S. patent application Ser. No. 09/037,417, filed Mar. 10, 1998 now U.S. Pat. No. 6,123,729.

BACKGROUND OF THE INVENTION

The present invention relates to knee prostheses for replacing the articular surfaces of a diseased or injured human knee. More particularly, the present invention relates to a knee prosthesis having an extended range of flexion.

Disease and trauma affecting the articular surfaces of the knee joint are commonly effectively treated by surgically replacing the articulating ends of the femur and tibia with prosthetic femoral and tibial implants, referred to as total knee replacements (TKR). These implants are made of materials that exhibit a low coefficient of friction as they articulate against one another so as to restore normal, pain free, knee function. Modern TKR's are tri-compartmental designs. That is, they replace three separate articulating surfaces within the knee joint; namely the patello-femoral joint and the lateral and medial inferior tibio-femoral joints. These implants are designed to articulate from a position of slight hyperextension to approximately 115 to 130 degrees of flexion. Such a tricompartmental design can meet the needs of most TKR patients even though the healthy human knee is capable of a range of motion (ROM) approaching 170 degrees. However, there are some TKR patients who have particular need to obtain very high flexion in their knee joint, usually as a result of cultural considerations. For many in the orient, and for some in the west, a TKR which permits a patient to achieve a ROM in excess of 150 degrees is desirable to allow deep kneeling, squatting, and sitting on the floor with the legs tucked underneath.

SUMMARY OF THE INVENTION

In order to meet such a high flexion requirement, the present invention provides a fourth articulating compartment, namely the superior posterior femoral condyles. All prior TKR designs ignore the superior posterior condyles. The articulating surface of the posterior condyles of prior TKR's continue their natural curves until the posterior condylar surface meets the interior posterior wall of the TKR fixation surface. Where the two surfaces meet, an edge is formed. For simply aesthetic reasons, the posterior superior edge of standard TKR's may have a small fillet. If such a TKR is able to articulate beyond 130 degrees at all, then the edge directly articulates against the tibial articulating surface which is usually made of ultra high molecular weight polyethylene (UHMWPE). Such a condition is contraindicated as it will lead to extremely small contact areas between the articulating components and could lead to exceptionally high wear rates. Such a condition could ultimately lead to the destruction and failure of the TKR. In the present invention, provision is made to add an additional articulating surface to each of the superior posterior femoral condyles so that at very high flexion angles, a proper articulation is maintained. Articulation along the superior posterior condylar surface of the present invention is intended. Thus, the superior posterior condyles represent a fourth compartment of articulation.

The superior posterior articulating surface is achieved by first increasing the thickness of the superior posterior condylar portion of the TKR femoral component to widen the superior posterior edge of the posterior condyle. Second, the newly created surface at the superior posterior condyle is smoothly rounded to provide an articular surface with no sharp changes in the surface contours. In one embodiment, the fourth articular compartment of this invention is provided in a one piece femoral design. In another embodiment, it is provided as a modular addition to an existing prior art femoral component. In another embodiment, the fourth compartment is combined with a posterior stabilized (PS) TKR design that includes a tibial post and cooperating femoral cam characterized by low engagement of the cam on the spine.

BRIEF DESCRIPTION OF THE DRAWINGS

FIG. 4 is a front plan view of an articular surface module according to the present invention.

FIG. 5 is a side plan view of the articular surface module of FIG. 4.

FIG. 6 is a top plan view of the articular surface module of FIG. 4 shown mounted on a femoral knee implant.

FIG. 7 is a side plan view of the articular surface module of FIG. 4 shown mounted on a femoral knee implant.

DETAILED DESCRIPTION OF THE INVENTION

FIGS. 1, 2, 3, 7 and 15 show embodiments of the femoral knee component of the present invention oriented at zero degrees of flexion. Unless otherwise noted, the geometric relationships of this invention are descriptive of a femoral knee implant in this orientation.

Figure 1:
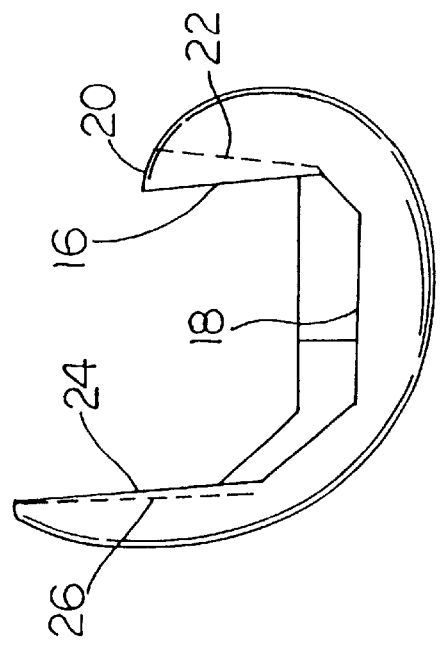
FIG. 1 is a side plan view of a femoral knee implant according to the present invention.

FIG. 1 depicts an exemplary one-piece femoral knee implant 1 according to the present invention. The implant 1 includes arcuate medial 2 and lateral (not shown) condyles joined together at their anterior aspects to form a patellar flange 4. Each of the media) 2 and lateral condyles includes a distal condyle 5, a posterior condyle 6, and a superior condyle 7. The patellar flange 4, the distal condyles 5, the posterior condyles 6, and the superior condyles 7 define a smooth articular surface extending around the exterior of the implant 1. The interior of the implant 1 is defined by a box 9. The box 9 includes an anterior box surface 10, a distal box surface 11 and a posterior box surface 12. The anterior 10 and distal 11 box surfaces are blended by an anterior chamfer surface 13. The distal 11 and posterior 12 box surfaces are blended by a posterior chamfer surface 14. The four compartment knee of the present invention accommodates flexion in the range of 165 degrees.

In order to provide the superior condyles 7 of the present invention, the superior aspect of the posterior condyles 6 is extended toward the anterior flange 4 to allow the articular surface to extend further around and back anteriorly than with prior femoral implants. Extending the superior aspect of the posterior condyle can be done in several ways. As shown in FIG. 1, the entire posterior condyle is thickened such that the posterior box surface 12 is further from the posterior condyle 6 exterior surface and nearer the anterior box surface 10. This widens the superior aspect of the posterior condyle so that the articular surface can be extended to form the superior condyle 7. Alternatively, posterior condyle 6 can be shortened by removing material from the superior aspect where the condyle begins to taper which will have the effect of leaving a thicker superior aspect that can be shaped into a superior condyle. Yet another alternative is to change the angle that the posterior box surface 12 makes with the distal box surface 11. By making the included angle between these two surface smaller, the superior aspect of the posterior condyle is made wider to provide for a superior condyle 7.

Figure 2:
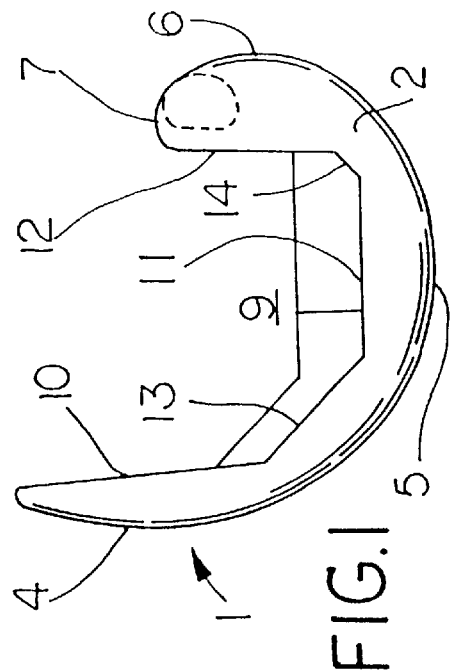
FIG. 2 is a side plan view of an alternative embodiment of the femoral knee implant according to the present invention.

Taking this angle change further leads to the embodiment of FIG. 2. Here, the angle between the posterior box surface 16 and the distal box surface 18 has been made less than 90 degrees to provide ample width for a superior condyle 20. The dashed line 22 depicts the angle of the posterior box surface of a typical prior art femoral component. In order for the femoral component to be easily implantable, posterior box surfaces 16 and the anterior box surface 24 must be parallel or slightly diverging toward the box opening. Therefore it may be necessary, as shown in FIG. 2, where the posterior box surface has been angled inwardly, to angle the anterior box surface 24 outwardly. The dashed line 26 depicts the angle of the anterior box surface of a typical prior art femoral component.

Figure 3:
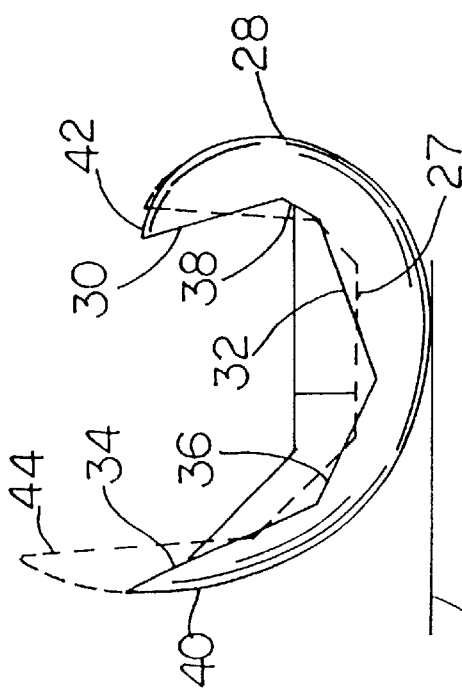
FIG. 3 is a side plan view of an alternative embodiment of the femoral knee implant according to the present invention.

FIG. 3 illustrates another alternative embodiment for moving the superior aspect of the posterior condyle 28 anteriorly. In this embodiment, the entire box; including the posterior surface 30, distal surface 32, anterior surface 34 and chamfers 36 and 38; is rotated about a medial-lateral axis thus shortening the anterior condyle 40 and extending the posterior condyle 28 anteriorly and slightly superiorly. A superior condyle 42 can then be formed at the superior aspect of the posterior condyle 28. The dashed lines 44 depict the box and articular surfaces of a typical prior art femoral component before the box is rotated.

In prior art implants the distal box surface 27 (dashed) is parallel to the tangent 31 of the distal condyles at their most prominent point. This helps a surgeon orient the femoral component at full extension. In the embodiment of FIG. 3, the box is rotated so that the distal surface 32 is angled relative to the tangent 31.

FIGS. 4–7 depict an alternative modular embodiment of the invention. The use of a modular add-on allows a conventional implant to be adapted for four compartment articulation. The implant 50 includes arcuate medial 52 and lateral 53 condyles joined together at their anterior aspects to form a patellar flange 54. Each of the medial 52 and lateral 53 condyles is made up of a distal condyle 55 and a posterior condyle 56. The patellar flange 54, the distal condyles 55 and the posterior condyles 56 define a smooth articular surface extending around the exterior of the implant 50. The articular surface terminates at the apexes 58 of the posterior condyles 56. The terminal portion of the articular surface is defined by the radius R. The interior of the implant 1 is defined by a box 59. The box 59 includes an anterior box surface 60, a distal box surface 61 and a posterior box surface 62. The anterior 60 and distal 61 box surfaces are blended by an anterior chamfer surface 63. The distal 61 and posterior 62 box surfaces are blended by a posterior chamfer surface 64.

FIGS. 4 and 5 depict an articular surface module 65. The module 65 includes a front surface 66, a back surface 67, a bottom surface 68, side surfaces 69, and a top surface 70. The back 67 and bottom 68 of the module 65 are shaped to seat against the posterior box surface 62 and posterior chamfer surface 64 respectively. The top surface 70 has an articular shape matching the articular surface of the implant 50 near the apexes 58. When the back 67 and bottom 68 of the module 65 are seated in the implant box 59, the top 70 of the module forms an extension of the articular surface, or a superior fourth compartment, as shown in FIGS. 6 and 7. The extended articular surface blends functionally with the articular surface to allow additional articulation of the femur relative to the tibia. Thus, a smooth transition is provided from articulation on the implant to articulation on the module. In tile embodiment shown in FIG. 7, the module 65 extends the radius R. A module is used similarly on both the medial and lateral posterior condyles. A through hole 71 in the module 65 and corresponding threaded holes in the posterior condyles allow the module 65 to be securely attached to the implant 50. Other well known means of attachment may also be used such as cement or clips.

The femoral component of the present invention accommodates deep flexion through the use of a fourth articular region. Other femoral features help to maximize the potential of this improved articular surface design. FIGS. 8–14 illustrate the femoral component 1 of FIG. 1 articulating with a tibial component 80. The tibial component 80 includes a spine 82 having an articular surface 84. The femoral component 1 includes a cam 90 having an articular surface 92. In flexion, the cam articular surface 92 bears on the spine articular surface 84. This spine/cam interaction creates a center for rotation of the femoral component relative to the tibial component and prevents anterior subluxation of the femoral component relative to the tibial component. The distance from the spine/cam contact to the top of the spine is called the "jump height" and is a measure of the subluxation resistance of a particular spine/cam combination because the cam would have to jump over the spine for subluxation to occur. In extreme flexion, such as that for which the present invention is designed, jump height is of increased concern. Likewise, bending of the spine is a concern due to increased loads during activities such as squatting. In many prior art implant designs, the cam is located relatively low compared to the top of the distal condyles. If these prior art knees are flexed deeply, the cam begins to ride up the spine and the jump height can be significantly shortened leading to an increased possibility of subluxation and an increased possibility of bending the spine because of the greater bending moment. In the present invention a high cam placement is used similar to the design of the NexGen® Complete Knee Solution manufactured and sold by Zimmer, Inc. By combining high cam placement with a fourth articular compartment, the extreme flexion potential of the knee is enhanced. Extreme flexion is facilitated while maintaining a safe level of subluxation resistance. As shown in FIGS. 8–14, the jump height increases from 90 degrees, FIG. 8, to approximately 130 degrees, FIG. 12. Beyond 130 degrees, the cam rises only slightly, thus maintaining a large jump height even in deep flexion.

Figure 15:
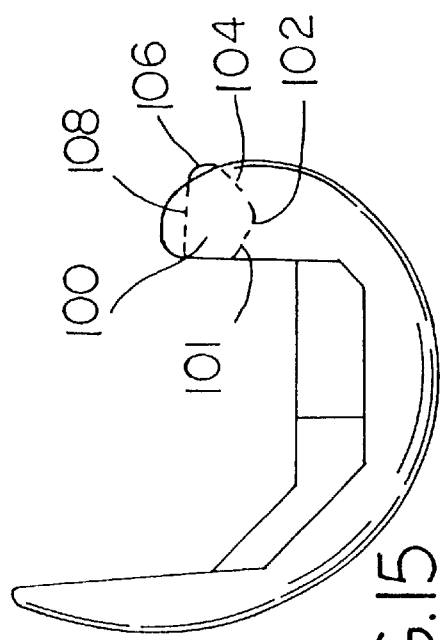
FIG. 15 is a side view of an alternative embodiment of the femoral knee implant according to the present invention.
Figures 8, 9, 10:
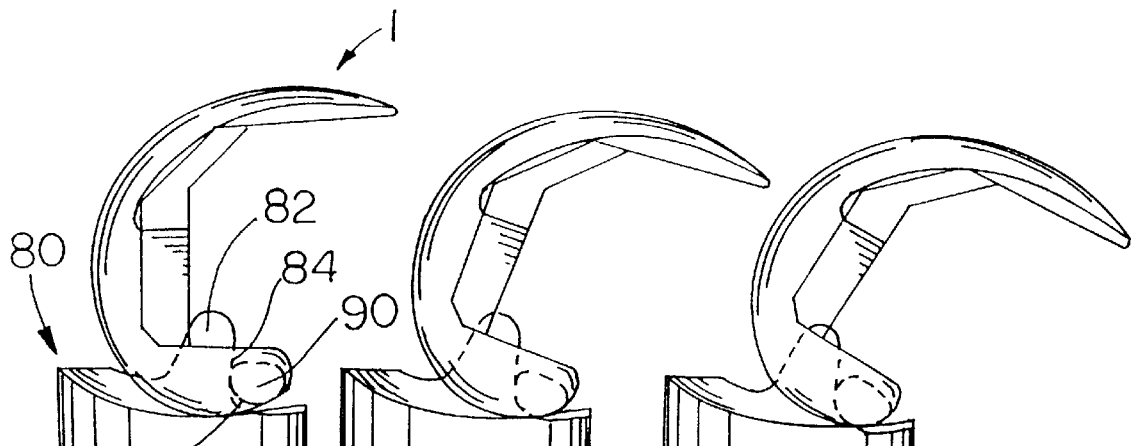
FIGS. 8–14 are side plan views of the femoral knee implant of FIG. 1 articulating with a tibial component of the present invention between 90 degrees and 160 degrees of flexion.
Figure 11:
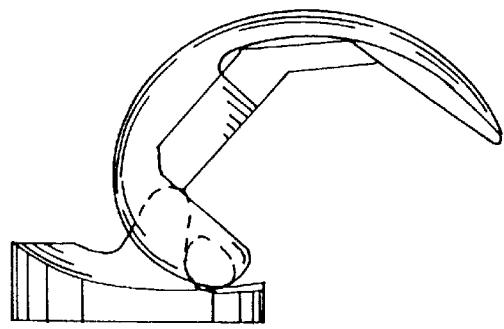
Figure 12:
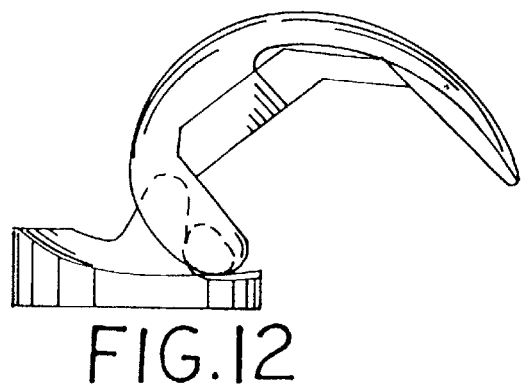
Figure 13:
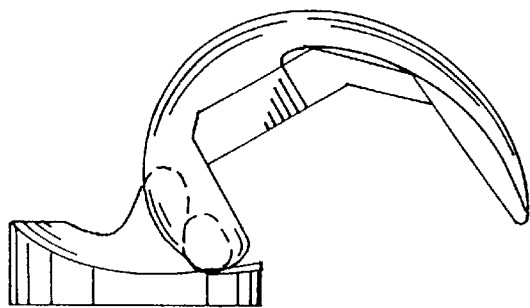
Figure 14:
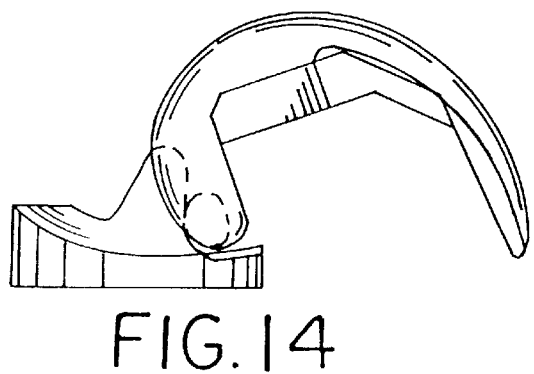
Figures 16, 17, 18:
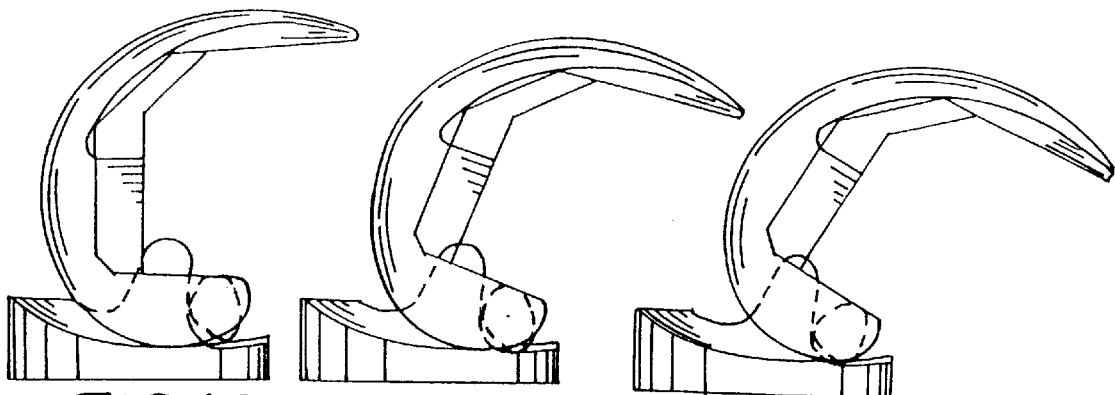
FIGS. 16–22 are side plan views of the femoral knee implant of FIG. 15 articulating with a tibial component of the present invention between 90 degrees and 160 degrees of flexion.
Figures 19, 20:
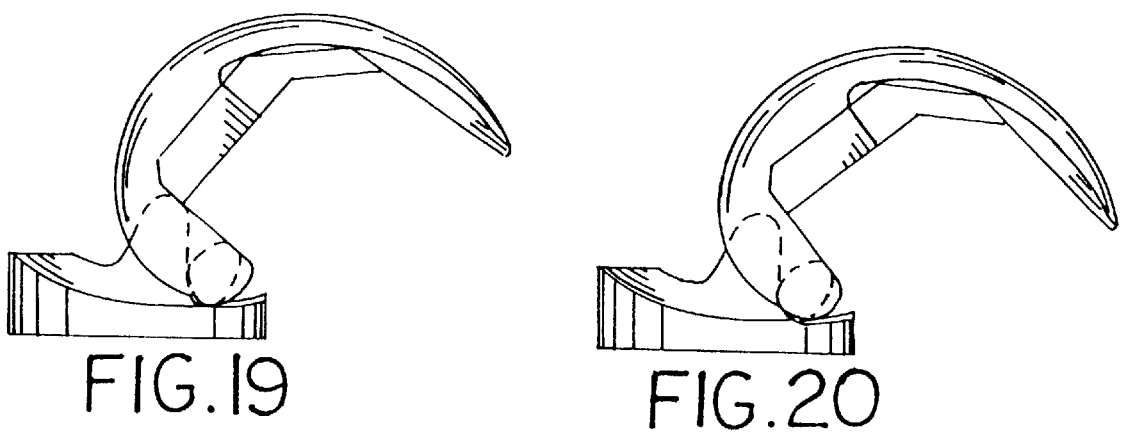

The embodiment of FIG. 15 further enhances the jump height of the spine cam articulation. The exemplary cam in FIGS. 1 and 8–14 is cylindrical at its functional articulating surface. It is placed far superiorly between the superior posterior condyles to increase jump height in flexion. To further enhance jump height, the cam in FIGS. 15–22 is made non-cylindrical, being made up of blended circles or other geometries. An exemplary non-cylindrical cam is shown in FIG. 15. The cam 100 includes a relatively flat portion 101, a first spine contact portion 102 having a first radius defining a circle, and a second spine contact portion 104 having a second radius defining a circle. The first spine contact portion 102 is an arc of the circle defined by the first radius. The second spine contact portion 104 is an arc of the circle defined by the second radius. The second spine contact portion extends further posteriorly than the perimeter of the circle defined by the first radius. In the embodiment shown in FIG. 15, the first and second spine contact portions form an ovoid articular surface 102, 104. Because the cam radius extends posteriorly, the second spine contact point is lower relative to the spine than it would otherwise be. The posterior extension of the cam 100 causes it to reach downwardly and contact the spine lower at higher angles of flexion as shown in FIGS. 16–20. The second contact portion 104 causes the femur to roll back in deep flexion to prevent the femoral bone, where it exits the posterior box, from impinging on the tibial articular surface. The top 108 of the cam 100 completes the cam profile.

The cam 100 alternatively includes a third spine contact portion 106, also shown in FIG. 15, having a third radius defining a circle. The alternative third spine contact portion projects beyond the condyles in order to maintain the proper femoral position relative to the tibia in deep flexion. The radius of the third portion 106, when present, forms the posterior most cam surface and the end of the cam articular surface.

Figures 21, 22:
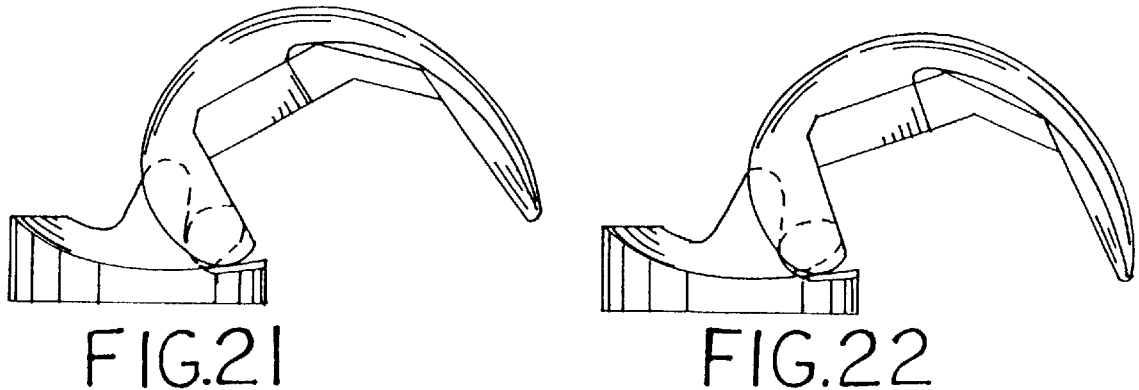

One way to achieve the described relationships between the spine contacting portions is to increase the radius of the cam 100 posteriorly from the first spine contact portion 102 to the second spine contact portion 104. The third spine contacting portion 106 would be made smaller than the second spine contacting portion 104 and would articulate as shown in FIGS. 21 and 22. Another way to achieve the inventive relationships is to offset the centers of the first and second radii in the anterior/posterior direction. Depending on the particular radius values and offset chosen, additional radii may be necessary to smoothly blend the first and second spine contacting surfaces.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A module for use with a femoral knee implant having an interior box and an articular surface for articulation with a tibial surface, the module comprising a back surface and a top surface, the back surface being shaped to seat against a portion of the box, the top surface being shaped to form an extension of the articular surface, the top surface blending functionally with the articular surface to allow articulation of the femoral implant on the tibial surface such that the knee implant can achieve about 165° of flexion between the femoral component and tibial component of the implant when the back surface is seated on a portion of the box.

2. A femoral knee implant for articulation with a tibial surface, the femoral knee implant comprising: an articular surface for articulation with the tibial surface; a box defining the interior surface of the implant; and a module comprising a back surface and a top surface, the back surface being shaped to seat against a portion of the box, the top surface being shaped to form an extension of the articular surface, the top surface blending functionally with the articular surface to allow articulation of the femoral implant on the tibial surface such that the knee implant can achieve about 165° of flexion between the femoral component and the tibial component of the implant when the back surface is seated on a portion of the box.

3. The femoral knee implant of claim 2 further comprising arcuate medial and lateral condyles joined together to form a patellar flange, each of the medial and lateral condyles including a distal condyle and a posterior condyle, the patellar flange, the distal condyles, and the posterior condyles defining the articular surface extending around the exterior of the implant, each posterior condyle including an apex at its highest point, the articular surface terminating at the apexes of the posterior condyles, the articular surface being defined by a radius R near the apexes, the top surface blending with the radius R to form a functionally smooth continuation of the articular surface.

* * * * *